(12) United States Patent
Obst et al.

(10) Patent No.: US 9,078,990 B1
(45) Date of Patent: Jul. 14, 2015

(54) DEVICES AND METHODS FOR TREATMENT OF FISTULAS AND COMPLEX WOUNDS

(71) Applicants: Andrew Thomas Obst, Scandia, MN (US); Maryanne Ruth Obst, Scandia, MN (US); David James Dries, Woodbury, MN (US)

(72) Inventors: Andrew Thomas Obst, Scandia, MN (US); Maryanne Ruth Obst, Scandia, MN (US); David James Dries, Woodbury, MN (US)

(*) Notice: Subject to any disclaimer, the term of this patent is extended or adjusted under 35 U.S.C. 154(b) by 1 day.

(21) Appl. No.: 13/750,154

(22) Filed: Jan. 25, 2013

Related U.S. Application Data

(60) Provisional application No. 61/633,046, filed on Feb. 3, 2012.

(51) Int. Cl.
| | |
|---|---|
| *A61M 1/00* | (2006.01) |
| *A61M 27/00* | (2006.01) |
| *A61F 13/00* | (2006.01) |
| *A61J 15/00* | (2006.01) |
| *A61M 25/02* | (2006.01) |
| *A61M 39/02* | (2006.01) |

(52) U.S. Cl.
CPC .......... *A61M 27/00* (2013.01); *A61F 13/00068* (2013.01); *A61J 15/0034* (2013.01); *A61J 15/0038* (2013.01); *A61M 1/0023* (2013.01); *A61M 2025/0233* (2013.01); *A61M 2039/027* (2013.01); *A61M 2039/0261* (2013.01)

(58) Field of Classification Search
CPC ............ A61J 15/0038; A61J 15/0034; A61M 2025/0233; A61M 2039/027; A61M 2039/0261; A61M 2039/0276; A61M 1/0088; A61M 1/008; A61M 1/08; A61M 2210/04

USPC ......... 604/327, 337, 313, 328, 317, 543, 174; 600/573

See application file for complete search history.

(56) References Cited

U.S. PATENT DOCUMENTS

| | | | |
|---|---|---|---|
| 5,636,643 A | 6/1997 | Argenta et al. | |
| 6,099,508 A * | 8/2000 | Bousquet | 604/175 |
| 7,708,724 B2 * | 5/2010 | Weston | 604/304 |
| 2008/0161778 A1 | 7/2008 | Steward | |
| 2008/0287892 A1 | 11/2008 | Khan et al. | |
| 2009/0131893 A1 | 5/2009 | Priest et al. | |
| 2009/0192467 A1 * | 7/2009 | Hansen et al. | 604/174 |
| 2009/0209917 A1 * | 8/2009 | Tanaka et al. | 604/174 |
| 2010/0145293 A1 | 6/2010 | Verhaalen | |
| 2010/0262095 A1 * | 10/2010 | Hall | 604/319 |

OTHER PUBLICATIONS

Goverman, et al., "The "Fistula VAC," a Technique . . .", The Journal of Trauma Injury, Infection, and Critical Care, vol. 60, No. 2, Feb. 2006, pp. 428-431.

Byrnes et al., "A Novel Technique to Skin Graft Abdominal Wall Wounds Surrounding Enterocutaneous Fistulas", Surgical Infections, vol. 11, No. 6, 2010, pp. 505-509.

Stremitzer, et al., "Successful bridging treatment and healing of enteric fistulae . . .", International Journal of Colorectal Disease, vol. 26, 2011, pp. 661-666.

Aguila, et al., "The Stool Shield: A Novel Approach to the Colo-Atmospheric Fistula", Journal of the American College of Surgeons, 2011, pp. e17-e19.

* cited by examiner

*Primary Examiner* — Leslie Deak
*Assistant Examiner* — Kai Weng
(74) *Attorney, Agent, or Firm* — Patterson Thuente Pedersen, P.A.

(57) ABSTRACT

An enteric fistula healing device, configured for application over a fistula or other wound to physically separate the fistula from the remainder of the wound area, such that any effluent from the intestine or bowel, or other enteric substances, that pass through the fistula are prevented from communicating with the wound area. The device is configured to collapse from a first height to a shorter second height.

12 Claims, 9 Drawing Sheets

DEVICES AND METHODS FOR TREATMENT OF FISTULAS AND COMPLEX WOUNDS

CROSS-REFERENCE TO RELATED APPLICATION

This application claims the benefit of U.S. provisional patent application Ser. No. 61/633,046, filed Feb. 3, 2012 and incorporated herein by reference.

BACKGROUND OF THE INVENTION

Complex abdominal wound care presents many challenges for healthcare professionals and patients. Particularly difficult to manage are enteric or intestinal fistulas which drain into open abdominal wounds. Fistulas are abnormal passages between organs that do not normally connect. In cases of enteric fistulas, a passage from the intestines to the surface of the skin allows intestinal effluent to spill onto a wound site and surrounding skin leading to infection, persistent tissue inflammation, and potentially sepsis. An enteric fistula can produce two to seven liters of effluent per day that must be contained and controlled if the wound is to heal.

Negative Pressure Wound Therapy (NPWT) uses a vacuum source to compress wound dressings and is commonly applied to complex abdominal wounds to promote healing. NPWT holds promise in managing open wounds with enteric fistulas; however the effectiveness of NPWT and other wound therapies have been limited by a persistent problem of wound dressing failure due to enteric fistula effluent fouling. As a NPWT vacuum is applied to a wound bed that includes an enteric fistula, the fistula's effluent is drawn into the NPWT dressing and across the entire wound bed. The effluent contamination causes tissue breakdown and infection, creates a loss of dressing vacuum seal as the system is overwhelmed with effluent, and necessitates frequent changes of expensive NPWT dressings.

A number of devices have been proposed to control the effluent from enteric fistulas, including U.S. patent publications 2010/0145293 to Verhaalen, 2008/0161778 to Steward, and 2008/0287892 to Khan et al.; however none of the prior art appears to have been commercialized in a way that has practical application at the bedside and enteric fistula wound dressing failure remains a common problem.

General disadvantages found with the prior art include: 1. Devices are not adaptable to comprehend the broad spectrum of enteric fistula and other wound types. Different stages of fistula development and healing have different effluent control demands that are difficult to address with devices that are not tailored to the specific wound. 2. Multi-component devices and multi-step device assembly create complexity for caregivers and may require specialized training or the expertise of a wound specialist. 3. Devices with rigid surfaces are very difficult to seal to the wound bed. Wound beds are dynamic and pliable surfaces and in practice we find that fistula effluent quickly finds it's way past rigid devices and wound dressing is fouled. Also, rigid devices tend to be uncomfortable for the patient and can aggravate the wound being treated. 4. Devices with thick containment walls and rigid flanges cannot be placed over fistulas and wounds that are in close proximity to the sides of the wound bed or underneath the edges of the abdominal wall and can cause tissue or other structural damage. 5. Devices that rely on ostomy adhesive to create a seal between the device and the wound site have poor longevity. In practice we find that these adhesives do not adhere well to wet, weeping wound beds and adhesion generally fails in 6 to 12 hours. As adhesion is lost, fistula effluent is drawn past the device and wound dressing is fouled.

An embodiment of the "isolation component" described in U.S. patent publication 2010/0145293 is demonstrated online at http://www.youtube.com/watch?v=fOGpffzZvSY for use on enteric fistula patients. However, this device has specific disadvantages. 1. The device is too complex for bedside nurses or homecare nurses to assemble without the help of a wound specialist. 2. The device fails to stay in the desired location when compressed with NPWT. 3. The device does not maintain desired form when compressed with NPWT and effluent is drawn past the device and wound dressing is fouled. 4. Caregivers often give up on the technique after repeated failures.

The present disclosure provides devices improved over the prior patent references and prior products.

SUMMARY

This disclosure describes devices to contain and control the effluent of enteric fistulas, other fistulas, stomas, and other wounds, comprises a containment vessel, walls which collapse when pressure is applied to the wound dressing, a primary vessel opening to fit over the wound being treated, and means for creating a seal around the primary vessel opening at the wound bed interface whereby effluent is contained.

A first particular embodiment of this invention is a device to manage effluent drainage from a fistula or other wound. The device has a fluid containment vessel having a first end and an interior volume defined by a sidewall configured to collapse from a first height to a second height less than the first height. The device has a primary vessel opening at the first end providing fluid communication to the interior volume, and a sealing ring proximate the primary vessel opening, the ring having an outer diameter greater than the vessel outer diameter at its first end. Such a device may include a secondary vessel opening at a second end of the fluid containment vessel, the secondary vessel opening also providing fluid communication to the interior volume and the primary vessel opening.

A second particular embodiment of this invention is a device that has a unitary, non-porous fluid containment vessel having a first end and a second end, and an interior volume defined by a sidewall of the vessel, which is configured to collapse from a first height to a second height less than the first height. The device has a primary vessel opening at the first end providing fluid communication to the interior volume and a secondary vessel opening at the second end providing fluid communication to the interior volume. The device further has a sealing ring proximate the primary vessel opening, the ring having an outer diameter greater than the vessel outer diameter at the first end. Such a device may further include a flange forming an appliance interface surface annular to the secondary vessel opening, and/or a skirt depending from the first end of the vessel, which may encircle the primary vessel opening. The sidewall may include radiused pleats to facilitate its collapse, and may be configured to collapse from a first height of at least 1 inch to a second height less than ½ inch.

Yet another particular embodiment of this invention is a method for controlling effluent drainage from a fistula by using a device comprising a collapsible side wall defining a primary vessel opening and having a sealing ring proximate the vessel opening. The method includes positioning the primary vessel opening and the sealing ring over a fistula in a wound bed, placing an open-cell foam over the device and the wound bed, and applying negative pressure to the open-cell foam to reduce the foam from a first height to a second height, and to reduce the side wall of the device from a first height to a second height.

Accordingly, this disclosure describes numerous enteric fistula devices having various aspects and advantages. The disclosure provides devices, which are simple in construction, to contain and control the effluent of enteric fistulas, other fistulas, stomas, and other wounds so dressings can be applied and changed by untrained bedside or homecare nurses. These devices seal to the wound bed and do not allow effluent to be drawn past the seal, even with negative pressure wound therapy (NPWT) or other wound care techniques, that might be used to extend dressing life and/or establish effective conditions for wound healing. The devices center and align themselves over a fistula or wound and hold themselves in the intended location, even with the application of NPWT and/or other wound therapies, during normal daily activity of the patient. The devices mitigate the need for ostomy adhesive, which reduces the frequency of wound dressing changes due to ostomy adhesive failure. The devices can be custom cut (e.g., at bedside) to best fit the device to irregular wound beds and positively center the device over a fistula or wound that is in close proximity to the sides of the wound bed or underneath the edges of the abdominal wall. The devices are flexible and collapse symmetrically when part of NPWT or other wound therapy to prevent deformation or buckling over and related aggravation of the fistula or wound. The devices isolate the fistula or wound from suction or vacuum, thus protecting the bowel or wound site from negative pressures. The devices are adaptable to a broad spectrum of enteric fistula and other wound types, and are less intrusive than plug-type devices which can aggravate fistulas and wounds and cause bowel injury. The devices can incorporate biologic solutions to provide a matrix for the growth of healthy granulation tissue and accelerate fistula and wound closure. Overall, the devices improve the healing process and thus improve the quality of patient life, by allowing patients to return to their normal life and work routines during the healing process.

These and various other features and advantages will be apparent from a reading of the following detailed description.

BRIEF DESCRIPTION OF THE DRAWING

The invention may be more completely understood in consideration of the following detailed description of various embodiments of the invention in connection with the accompanying drawing, in which.

DETAILED DESCRIPTION OF THE INVENTION

Figure 1A:
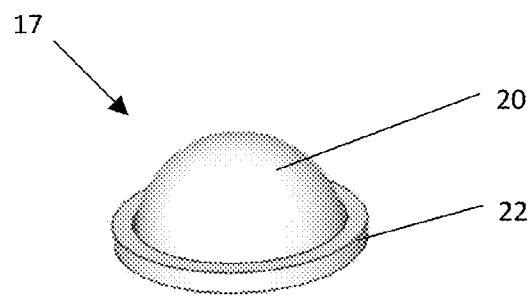
FIG. 1A is a perspective view of a device according to this disclosure.

The present disclosure provides various embodiments of enteric fistula healing devices, configured for application over a fistula or other wound to physically separate the fistula from the remainder of the wound area, such that any effluent from the intestine or bowel, or other enteric substances, that pass through the fistula are prevented from communicating with the wound area.

All of the devices have a unitary or one-piece fluid containment vessel for receiving and managing intestine effluent, either by containing the effluent or by managing its flow through the vessel. The vessel has an interior volume defined by sidewall(s) and has a first end and an opposite second end. The device, particularly the fluid containment vessel, is adapted to be placed in surrounding relationship relative to a wound site, and particularly, in one embodiment, to surround an enteric fistula. At least the first end of the device is open, forming a primary vessel opening. At the open first end, around the vessel opening, is a seating or sealing ring, preferably a continuous ring, having an outer diameter greater than the outer diameter of the vessel. The second end of the vessel may additionally be open to the interior volume, forming a secondary vessel opening.

The fluid containment vessel is collapsible, from a first height to a second height less than the first height. When the device is in a relaxed state (e.g., not installed on a wound), the vessel has its first height, and when the device is in its collapsed or "use" state (e.g., installed on a wound), the vessel has its second height. In some embodiments, the first height is at least 1 inch, and can be at least 1½ inches. The second height is less than the first height, in some embodiments no more than ½ inch, in other embodiment no more than ⅜ inch, and in other embodiments no more than ¼ inch. The vessel height may additionally or alternately reduce 50% from its relaxed state to its collapsed state, or at least 50%, such as about 65% percent. The rigidity and thus collapsibility of the vessel can be adjusting by modifying the material and thickness of the vessel wall, and by including features such as ribs or pleats in the wall. The diameter (inner diameter, outer diameter, or both) of the fluid containment vessel may increase or decrease, depending on the mode of collapse of the vessel wall.

As used herein, "collapse", "collapsible" and variations thereof means that the structure, particularly the side wall structure of the vessels, folds, falls in, crumbles, or otherwise decreases upon itself. In some embodiments of "collapse", the wall may fold upon itself to form a region that has a doubled wall; however, embodiments where two discrete (unconnected) pieces are slid or otherwise moved in overlapping relation to each other is not considered to be a collapse of the pieces. In some embodiments of "collapse", the wall may twist or rotate about the longitudinal axis of the vessel, thus forming folds, creases and the like in the wall.

In use, the device is placed in a wound bed such that the wall of the fluid containment vessel surrounds a fistula or other wound opening. By being so positioned, the device separates the fistula from the remainder of the wound area. This separation prevents any intestinal effluent or other enteric substance passing out of the fistula from coming into contact with the wound area surrounding the fistula, as the effluent will be at least initially retained within the interior volume of the vessel. This promotes healing of the wound bed and lowers the chances for infection.

In the following description, reference is made to the accompanying drawings that form a part hereof and in which are shown by way of illustration several specific embodiments. The following reference numbers are used throughout the drawings:

| | |
|---|---|
| 17 | device |
| 18 | primary vessel opening sized and shaped to fit over wound or fistula |
| 19 | cuttable, flexible flange around the perimeter of the primary vessel opening |
| 20 | flexible fluid containment vessel, cap, or dome |
| 21 | electrical leads |
| 22 | seating or sealing ring, e.g., open-cell foam |
| 23 | electric power supply |
| 24 | vessel wall |
| 25 | biologic membrane |
| 26 | bulb on the inside of the vessel |
| 28 | ribbing in the vessel wall |
| 29 | pleats in the vessel wall |
| 30 | flexible annular skirt(s) concentric to the primary vessel opening |
| 31 | recessed groove in the vessel wall |
| 32 | channel or perforation through an interior seal to the concentric pressure equalization chamber |
| 33 | wound fluid pressure inside device $P_{wound}$ |
| 34 | pressure equalization chamber with fluid pressure $P_c$ |
| 35 | fluid pressure in dressing outside of the device $P_{dressing}$ |
| 40 | device with outlet |
| 42 | integral tube |
| 46 | secondary vessel opening |
| 60 | device with intubation |
| 62 | internal drainage management tube |
| 64 | airway or drainage path |
| 66 | stopper feature |
| 67 | drainage management tube perforations |
| 69 | managed drainage path |
| 70 | device with appliance interface |
| 72 | flexible fluid containment vessel, tube, or cylinder |
| 74 | appliance interface surface |
| 75 | wound drape cutter ring |
| 77 | wound drape cutter ring flange |
| 79 | wound drape cutter ring edge |
| 80 | cuttable flange around the perimeter of the secondary vessel opening |
| 85 | alternative seating or sealing ring, with different thickness, size and shape |
| 86 | flexible hook(s) |
| 90 | device with appliance interface |
| 92 | flexible fluid containment vessel, tube, or cylinder |
| 94 | vessel wall |
| 100 | adhesive wound drape |
| 102 | hole through adhesive wound drape |
| 104 | wound dressing |
| 106 | tunnel or cavity in wound dressing |
| 108 | enteric fistula or other wound |
| 110 | abdominal tissue |
| 112 | wound bed |
| 114 | intestine |
| 116 | intestinal content or effluent |

The following description provides additional specific embodiments. It is to be understood that other embodiments are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples provided below.

Unless otherwise indicated, all numbers expressing feature sizes, amounts, and physical properties are to be understood as being modified by the term "about." Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Figure 1B:
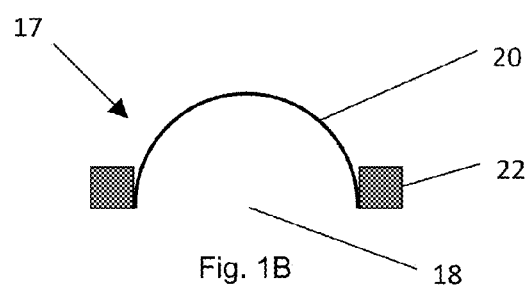
FIG. 1B is a cross-sectional side view of the device of FIG. 1A.

A first embodiment of a device for enteric effluent management is shown in FIGS. 1A and 1B as device 17. This particular embodiment manages the effluent by containing the effluent, and inhibiting the effluent from draining or leaking from the bowel or intestine.

Device 17 has a flexible fluid containment vessel, cap, or dome 20 defining a primary vessel opening 18 shaped and sized or otherwise configured to fit over wound or fistula. Encircling opening 18 and the perimeter of dome vessel 20 is a sealing or seating ring 22, which has an outer diameter greater than the outer diameter of dome vessel 20. Ring 22 may be formed of any number of materials, but a preferred material for this embodiment is an open-celled foam. Device 17 is configured to collapse, preferably symmetrically and evenly, from the top of its dome to ring 22 and opening 18. When in its collapsed state, device 17 retains its overall form, defining a volume for containment of fluid, when employed as part of a compression dressing to prevent deformation or buckling over and related aggravation of the fistula or wound. Changing the material and/or thickness of vessel wall 24 controls the degree of collapse.

Figure 1C:
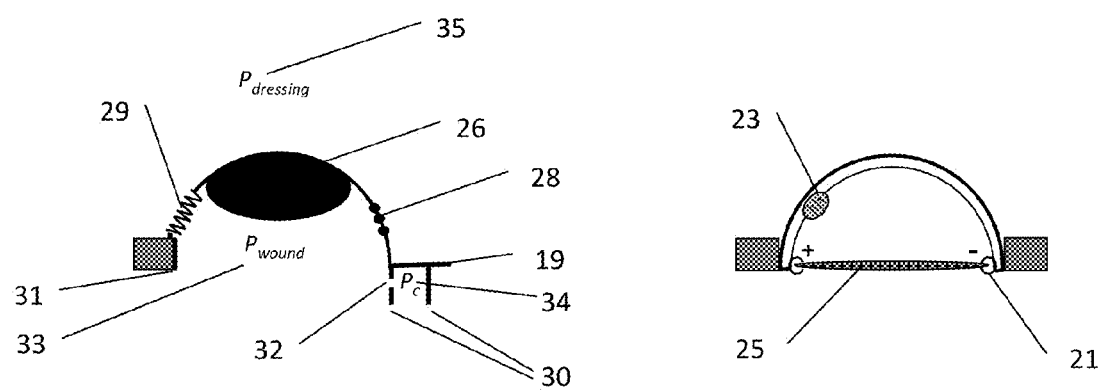
FIG. 1C is a cross-sectional side view of an alternative embodiment of the device of FIG. 1A.
Figure 1D:
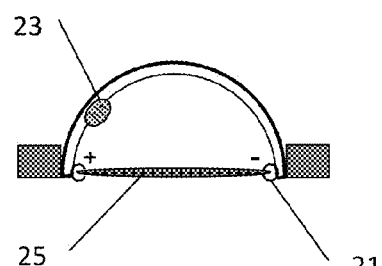
FIG. 1D is a cross-sectional side view of another alternative embodiment of the device of FIG. 1A.

Various optional features for device 17 are shown in FIGS. 1C and 1D. For example, a bulb 26 may be added on an inner surface of or in the interior volume of dome vessel 20 to help seal fistulas and wounds. A collapsible or physically deformable structure, such as ribbing 28 or pleats 29, may be present in vessel wall 24; such structure may improve the symmetrical collapse of dome vessel 20. A groove 31 may be formed in vessel wall 24 as a retainer for ring 22. A membrane 25 (e.g., a biologic membrane) may be incorporated inside dome vessel 20, as shown in FIG. 1D, to support the growth of healthy granulation tissue and accelerate fistula and wound closure. To further accelerate the healing, an electric power supply 23 with electrical leads 21 can be connected to biologic membrane 25 or the wound bed to accelerate healing with electrical stimulation.

Returning to FIG. 1C, device 17 may include one or more flexible skirt(s) 30 at least partially encircling opening 18 in addition to or in lieu of ring 22 to act as a seating mechanism of device 17. Skirt(s) 30 may be cuttable or otherwise configurable to be tailored to the specific application. Skirt(s) 30 positively center device 17 over the fistula or wound to inhibit movement of device 17 during dressing compression or normal daily activity of the patient. Skirt(s) 30 may be custom cut for each patient (e.g., at bedside) to adapt device 17 to best fit irregular fistula or wound walls and mechanically block effluent from being drawn past device 17 and contaminating the surrounding wound dressing. Skirt(s) 30 further create a positive seal with the wound bed to contain effluent and direct it away from the fistula or wound and other nearby tissue to promote healing. And further, skirts(s) 30 isolate the fistula or wound from negative pressure, vacuum or suction and protect the bowel or wound site.

In an embodiment utilizing two skirts 30, as in FIG. 1C, a concentric pressure equalization chamber 34 is formed between two skirts 30. A channel or perforation 32 in the inner skirt 30 allows the fluid pressure $P_c$ in the concentric pressure equalization chamber 34 to equalize with the high wound fluid pressure $P_{wound}$ 33 inside device 17. Such equalization between chamber 34 and the higher wound pressure reduces the draw of effluent from the wound toward the concentric chamber 34 and thus reduces seal failure if the wound has sudden spikes in effluent fluid pressure. Without equalization, the pressure in chamber 34 could drop as low as the dressing pressure $P_{dressing}$ 35 outside of device 17, undesirably drawing effluent from the wound towards chamber 34 and increasing the possibility of seal failure.

Also in FIG. 1C, a flexible flange 19 is present around the perimeter of the primary vessel opening 18, to create a positive seal with the wound bed. The surface of flange 19 may be textured to help seat device 17 in wound bed and mitigate need for separate wound adhesives. Flange 19 can be custom cut (e.g., at bedside) to adapt device 17 to fit irregular wound beds and positively center device 17 over a fistula or wound that is in close proximity to the sides of the wound bed or underneath the edges of the abdominal wall.

Any of these various alternate options shown in FIGS. 1C and 1D may be used alone or in any combination on device 17.

Figure 2A:
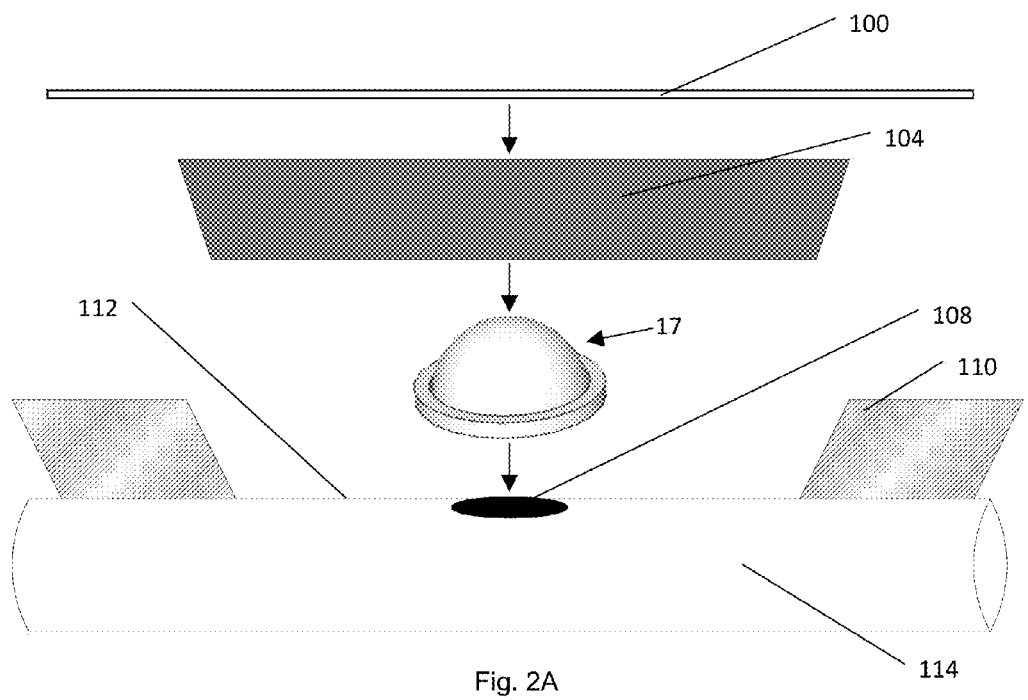
FIG. 2A is an exploded view of the device of FIG. 1A employed on an enteric fistula.
Figure 2B:
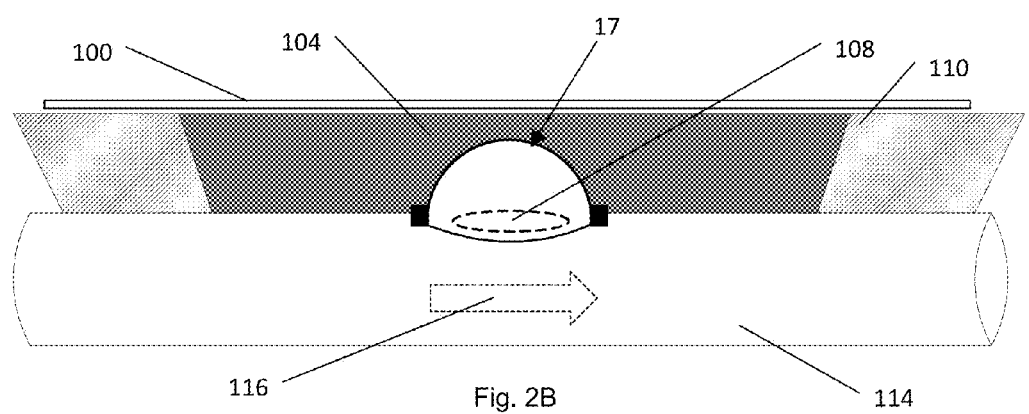
FIG. 2B is the assembled view of FIG. 2A.

FIGS. 2A and 2B illustrate use of device 17 with an enteric fistula 108 present in intestine 114. The objective in this employment of device 17 is to encourage content 116 (e.g., effluent) of intestine 114 to flow past the fistula or wound site 108, allowing wound bed healing and eventual fistula closure. Device 17, in essence, seals or caps fistula 108, inhibiting the escape of effluent 116 from intestine 114.

FIG. 2A shows the application of device 17 over fistula 108. Device 17 is sized to have a diameter greater than that of fistula 108; for example, a gap of approximately 6 mm around the margin base of fistula 108 is suitable, although larger and smaller gaps may be used. After placement, as in FIG. 2B, device 17, fistula 108 (covered by device 17) and the entire wound bed are covered with a wound dressing 104, such as Negative Pressure Wound Therapy (NPWT) open-celled foam. Wound dressing 104 is typically sealed with an adhesive wound drape 100 to the surrounding abdominal tissue 110 and negative pressure or vacuum is typically initiated to compress wound dressing 104 and device 17.

Figure 3A:
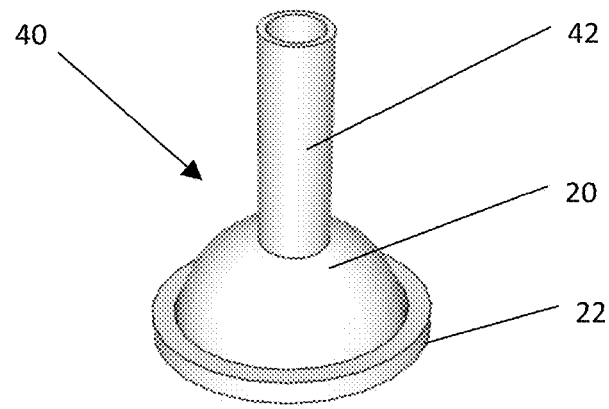
FIG. 3A is a perspective view of an embodiment of a device with an outlet according to this disclosure.
Figure 3B:
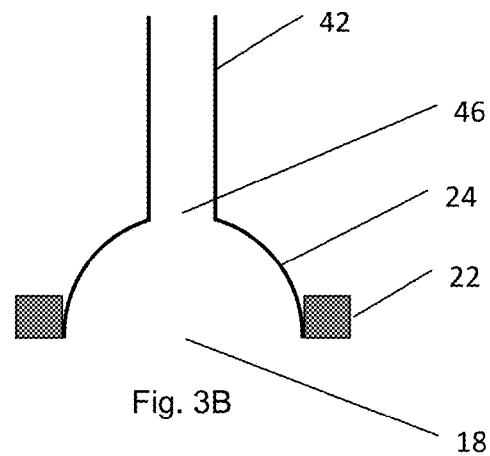
FIG. 3B is a cross-sectional side view of the device of FIG. 3A.
Figure 3C:
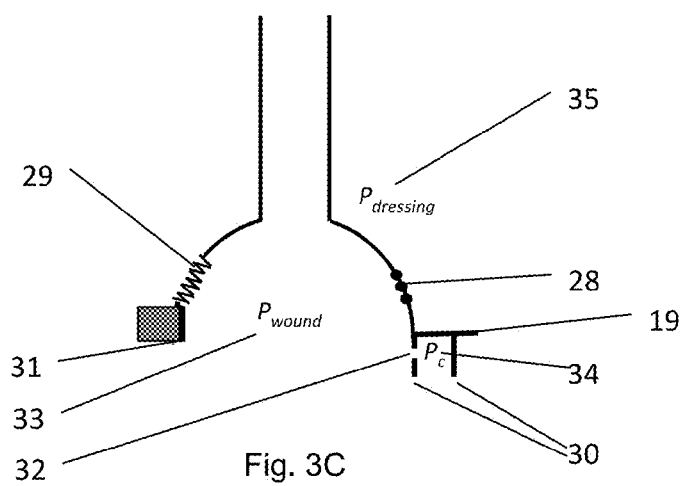
FIG. 3C is a cross-sectional side view of an alternative embodiment of the device of FIG. 3A.

A second embodiment of a device for enteric effluent management is shown in FIGS. 3A and 3B as device 40. Device 40 is similar to and has many of the same features as device 17 of FIGS. 1A and 1B (e.g., dome vessel 20, primary vessel opening 18, vessel wall 24 and ring 22), except device 40 includes a tube 42 attached to the internal volume of fluid containment vessel 20. Device 40, with tube 42, manages the drainage of effluent from the bowel or intestine. Tube 42 is preferably fixed to vessel wall 24 or may be integrally formed thereto. Tube 42 forms a secondary vessel opening 46 (seen in FIG. 3B) to the interior cavity of vessel 20. At its other end, tube 42 provides a vent.

Similar to device 17, device 40 may include any or all of the following optional features. Device 40 may include ribbing 28 or pleats 29 in vessel wall 24 to improve symmetrical collapse of vessel wall 24 when collapsed, and/or may include a groove 31 in wall 24 as a retainer for ring 22. One or more flexible skirt(s) 30 concentric to opening 18 may be present as a seating and/or sealing mechanism. Two skirts 30 can form a concentric pressure equalization chamber 34, having an aperture or hole 32 in the inner skirt 30, to equalize the fluid pressure $P_c$ in chamber 34 with the high wound fluid pressure $P_{wound}$ 33 inside vessel 20 of device 40. Without equalization, the pressure in chamber 34 could drop as low as the dressing pressure $P_{dressing}$ 35 outside device 40, drawing effluent from the wound towards chamber 34 and increasing the possibility of seal failure. A flexible flange 19 may additionally or alternately be present.

Figure 4A:
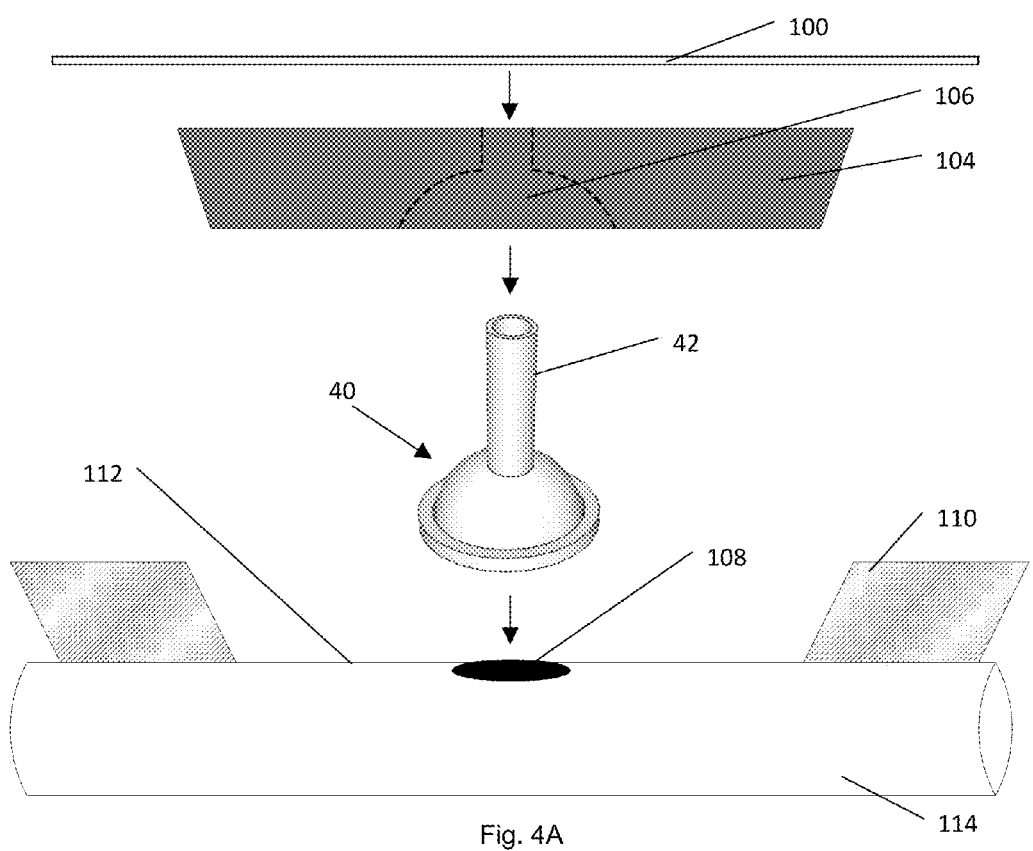
FIG. 4A is an exploded view of the device of FIG. 3A employed on an enteric fistula.
Figure 4B:
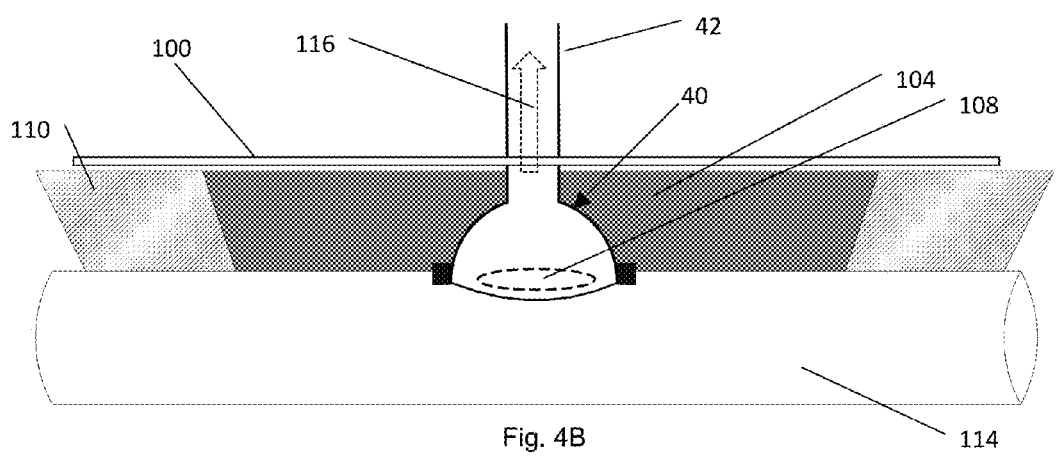
FIG. 4B is the assembled view of FIG. 4A.

FIGS. 4A and 4B illustrate use of device 40 with an enteric fistula 108 present in intestine 114. The objective in this employment of device 40 is to provide a drainage path via tube 42 for effluent 116 from intestine 114 when flow volumes from the fistula or wound site 108 are too high for capping.

FIG. 4A shows device 40 with venting tube 42 over fistula 108. Device 40 is sized to have a diameter greater than that of fistula 108; for example, a gap of approximately 6 mm around the margin base of fistula 108 is suitable, although larger and smaller gaps may be used. After placement, device 40, fistula 108 (covered by device 40) and the entire wound bed are covered with a wound dressing 104, such as open-celled foam, having a cavity 106 formed therein to accommodate device 40; a portion of tube 42 preferably is not covered by dressing 104 but extends above the level of dressing 104. Wound dressing 104 is typically sealed with an adhesive wound drape 100 to the surrounding abdominal tissue 110 and negative pressure or vacuum is typically initiated to compress wound dressing 104 and device 40. Tube 42 is then connected to a gravity drainage appliance or gentle suction to collect effluent 116.

Figure 5A:
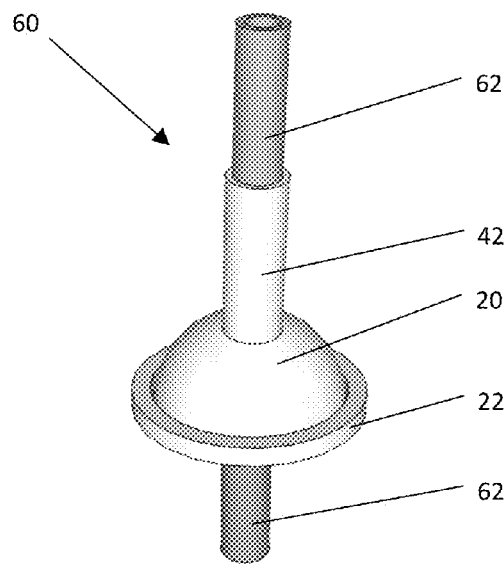
FIG. 5A is a perspective view of an embodiment of a device with intubation according to this disclosure.
Figure 5B:
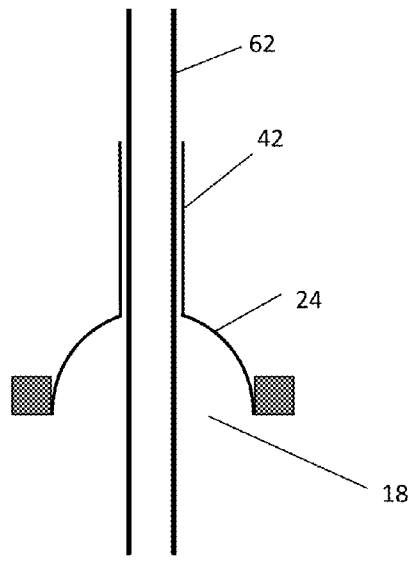
FIG. 5B is a cross-sectional side view of the device of FIG. 5A.

A third embodiment of a device for enteric effluent management is shown in FIGS. 5A and 5B as device 60. Device 60 is similar to and has many of the same features as device 40 of FIGS. 3A and 3B (e.g., dome vessel 20, primary vessel opening 18, vessel wall 24, ring 22 and tube 42), except device 60 includes a mechanism for intubating the fistula or wound.

Device 60 includes an internal drainage management tube 62 present within the drainage tube 42. The internal drainage management tube 62 may be fixed or may slide freely inside tube 42. Tube 42 is preferably sufficiently long to extend above the venting end of tube 42 and into the interior volume of dome vessel 20, preferably through vessel 20 and past vessel opening 18.

Figure 5C:
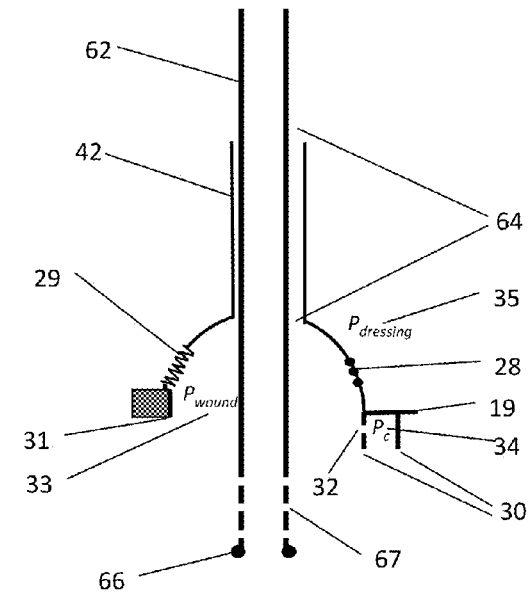
FIG. 5C is a cross-sectional side view of an alternate embodiment of the device of FIG. 5A.

Device 60 may include various optional features, illustrated in FIG. 5C. A venting path or channel 64 may be present between drainage management tube 62 and tube 42; channel 64 can be either or both an airway or effluent drainage path. Tube 62 may include perforation(s) 67 in the portion of tube 62 present in vessel 20 to improve drainage. Perforation(s) 67 may be at or near a stopper feature 66 at the base of the integral tube 42 that inhibits movement of tube 62 in the direction out from vessel 20. Additionally, stopper feature 66 can seal channel 64, thus inhibiting airflow or drainage between drainage management tube 62 and tube 42.

Similar to device 40, device 60 may include any or all of the following optional features: ribbing 28 or pleating 29 in vessel walls 24; a groove 31 in vessel wall 24; one or a plurality of skirt(s) 30, with an aperture or perforation 32, that can form a concentric pressure equalization chamber 34 to equalize the fluid pressure $P_c$ in chamber 34 with the high wound fluid pressure $P_{wound}$ 33; and a flange 19 around the perimeter of opening 19. These features may facilitate to positively center device 60 over the fistula or wound so that device 60 will not move during dressing compression or during normal daily activity of the patient.

Figure 6A:
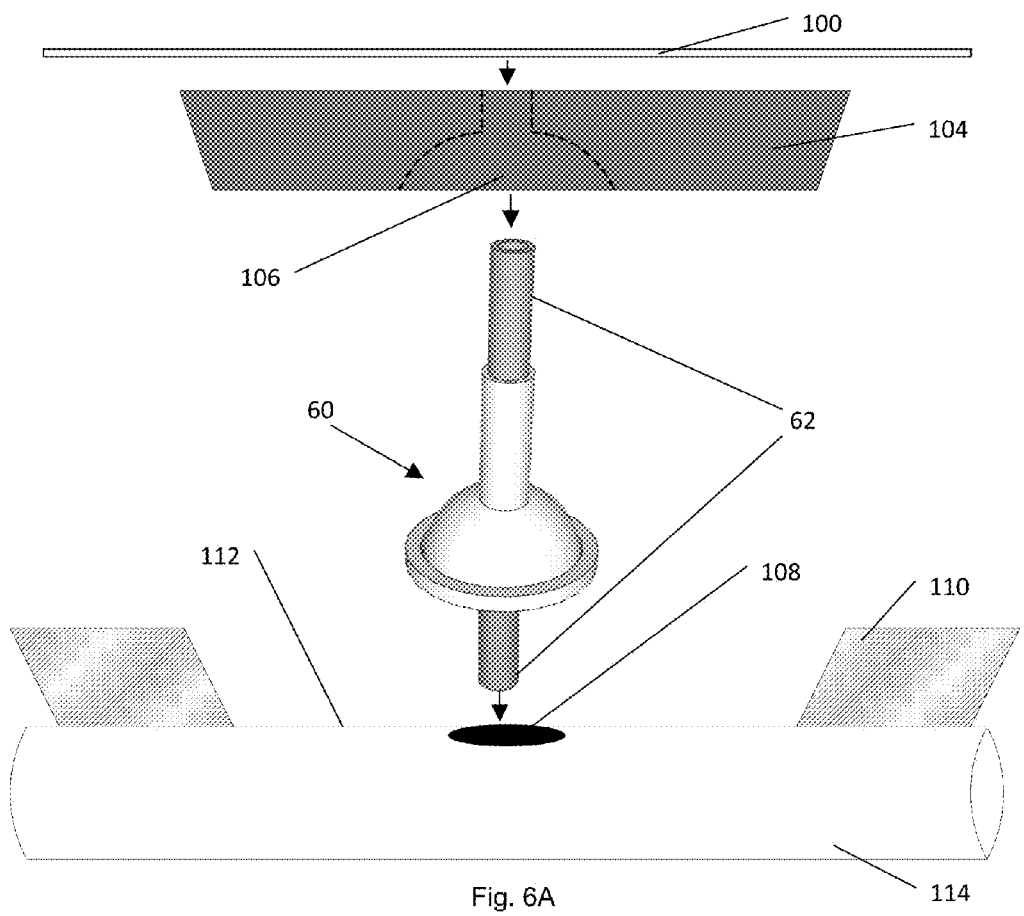
FIG. 6A is an exploded view of the device of FIG. 5A employed on an enteric fistula.
Figure 6B:
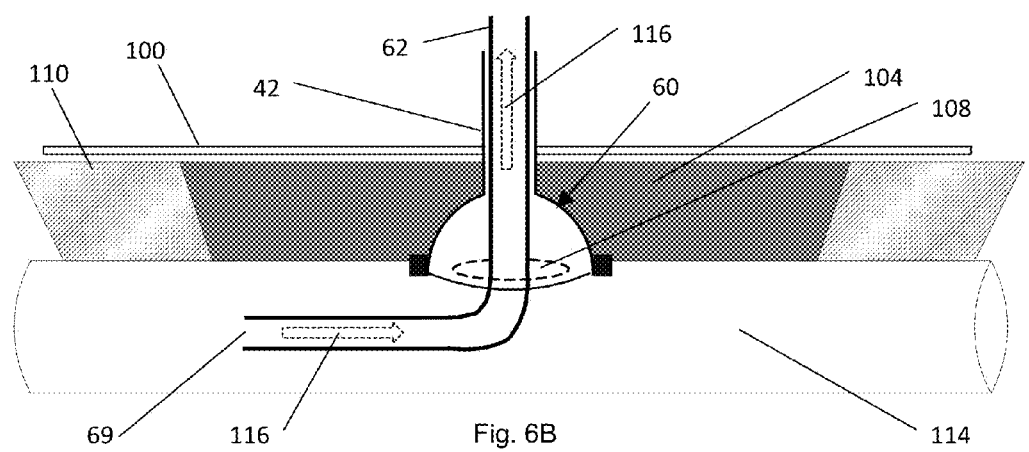
FIG. 6B is the assembled view of FIG. 6A.

FIGS. 6A and 6B illustrate use of device 60 with an enteric fistula 108 present in intestine 114. The objective in this employment of the device with intubation is to create a managed drainage path 69 for effluent 116 to pass from intestine 114 through fistula or wound site 108.

FIG. 6A shows the application of device 60 over fistula 108. Device 60 is sized to have a diameter greater than that of fistula 108; for example, a gap of approximately 6 mm around the margin base of fistula 108 is suitable, although larger and smaller gaps may be used. During placement, drainage management tube 62 is gently inserted into fistula 108 and intestine 114 is intubated. Gentle suction is applied to drainage management tube 62 as device with intubation 60 is carefully placed over fistula 108. After placement, as shown in FIG. 6B, device 60, fistula 108 (covered by device 60) and the entire wound bed 112 are covered with a wound dressing 104, such as open-celled foam, with a cavity 106 formed therein to accommodate device 60; a portion of tube 42 and tube 62 preferably is not covered by dressing 104 and extends above the level of dressing 104. Wound dressing 104 is typically sealed with an adhesive wound drape 100 to the surrounding abdominal tissue 110 and negative pressure or vacuum is typically initiated to compress wound dressing 104 and device 60. The exposed end of drainage management tube 62 is then connected to a gravity drainage appliance or gentle suction. The internal drainage management tube 62 is used to manage effluent 116 from intestine 114 and can be retracted incrementally to allow healing of the fistula. Tube 42 is available to remove effluent 116 from fistula site 108 when needed or desired.

Figure 7A:
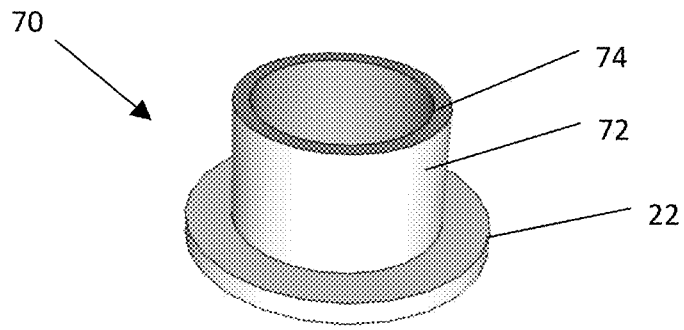
FIG. 7A is a perspective view of a device with appliance interface according to this disclosure.
Figure 7B:
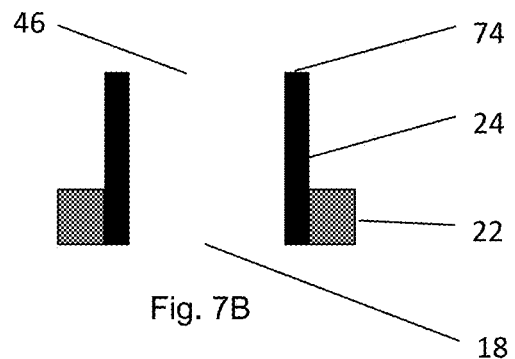
FIG. 7B is a cross-sectional view of the device of FIG. 7A.

A fourth embodiment of a device for enteric effluent management is shown in FIGS. 7A and 7B as device 70 having an appliance interface. Device 70 is designed to collapse symmetrically and maintain form when employed as part of a compression dressing to prevent deformation or buckling over and related aggravation of the fistula or wound.

Device 70 has a flexible fluid containment vessel 72, formed by vessel walls 24, and may be a tube, cylinder or other feature, with a primary vessel opening 18 configured to fit over a wound or fistula. A sealing or seating ring 22 is attached to vessel 72 at the perimeter of vessel opening 18. Ring 22 has an outer diameter greater than the outer diameter of vessel 72, and in some embodiments, ring 22 may be formed from foam, e.g., open-cell foam.

Opposite primary vessel opening 18 is a secondary vessel opening 46, which may be axially aligned with primary opening 18. Secondary opening 46 has an appliance interface surface 74 configured to provide a bonding surface for adhesive films and a seating area for appliances that capture fistula, stoma and wound effluent. Interface surface 74 may be flat or may be textured.

Figure 7C:
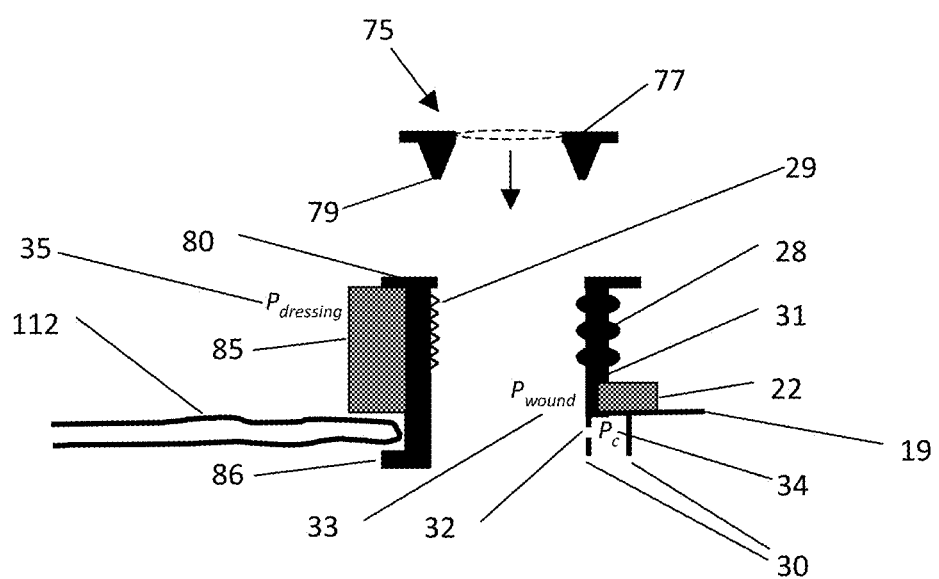
FIG. 7C is a cross-sectional side view of an alternative embodiment of the device of FIG. 7A.

Device 70 may include various optional features, illustrated in FIG. 7C. Separate from, but used in conjunction with wound drape cutter ring 75, a wound drape cutter ring 75 that snaps on to vessel 72 at interface surface 74 may be present. Cutter ring 75 has a cutting feature 79 (e.g., a continuous edge or point) designed to safely wound drape when cutter ring 75 is snapped on to appliance interface surface 74. Cutter ring 75 further has a flange 77 that provides a surface for seating appliances that capture fistula and wound effluent. Further, appliance interface surface 74 can be widened by extending a flange 80 around the perimeter of secondary vessel opening 46 to create additional surface area for bonding adhesive wound drapes and seating appliances that capture fistula and wound effluent. Flange 80 can be trimmed as needed to adapt device 70 to best fit irregular wound beds and positively center device 70 over a fistula or wound that is in close proximity to the sides of the wound bed or underneath the edges of the abdominal wall. Still further, sealing ring 22 can be increased in height and/or diameter to create ring 85, configured to fit specific wound dressing applications, such as extending optionally to flange 80 or to surface 74. Device 70 may additionally include a hook or hooks 86 extending circumferentially around primary vessel opening 18, to hook into the mouth of a wound or fistula as a retention mechanism.

Similar to previously described devices, device 70 may include any or all of the following optional features: ribbing 28 or pleating 29 in vessel walls 24; a groove 31 in vessel wall 24; one or a plurality of skirt(s) 30, with an aperture or perforation 32, that can form a concentric pressure equalization chamber 34 to equalize the fluid pressure $P_c$ in chamber 34 with the high wound fluid pressure $P_{wound}$ 33; and a flange 19 around the perimeter of opening 18. These features may facilitate to positively center device 60 over the fistula or wound so that device 60 will not move during dressing compression or during normal daily activity of the patient.

Figure 8A:
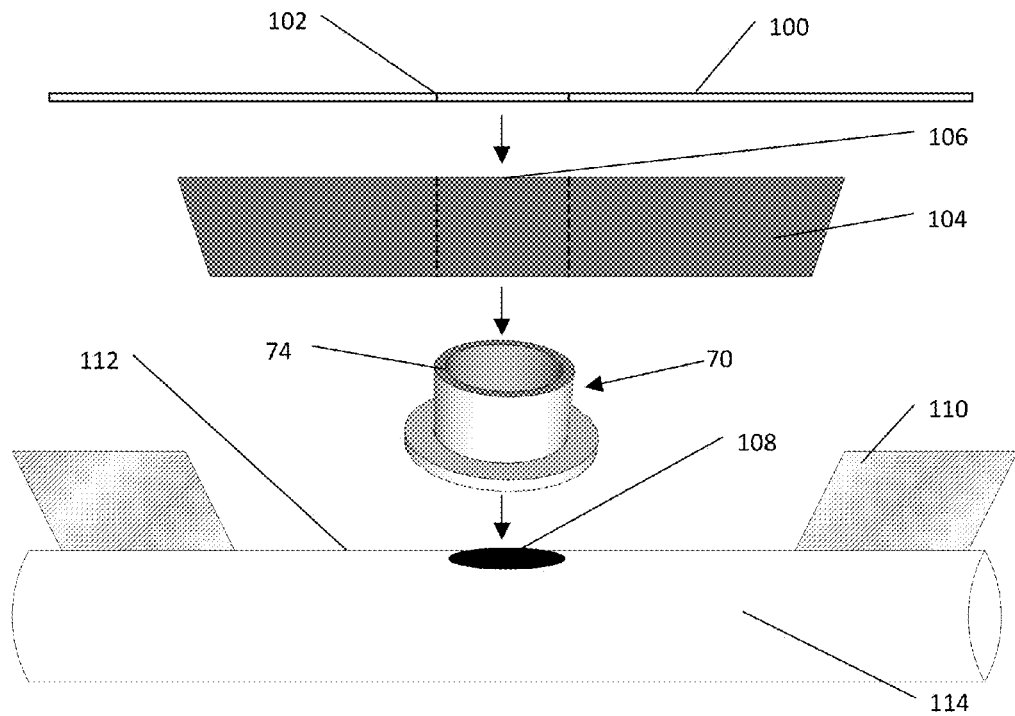
FIG. 8A is an exploded view of the device of FIG. 7A employed on an enteric fistula.
Figure 8B:
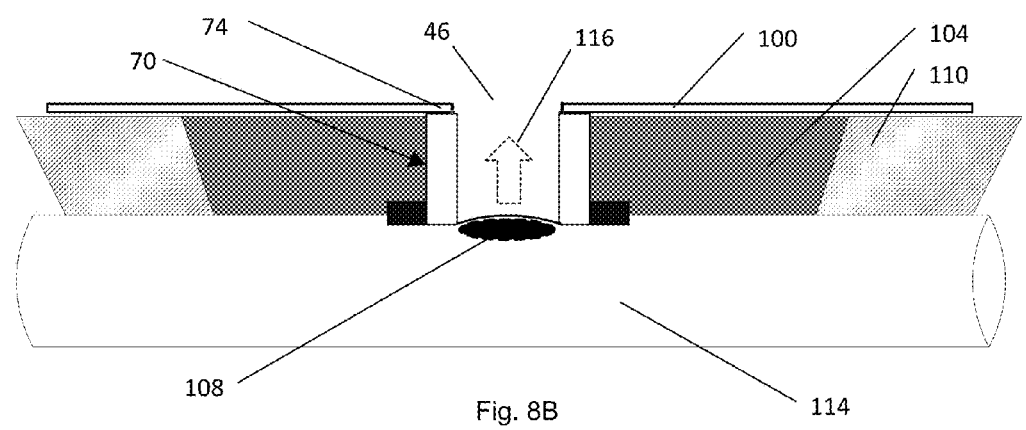
FIG. 8B is the assembled view of FIG. 8A.

FIGS. 8A and 8B illustrate use of device 70 with an enteric fistula 108 present in intestine 114. The objective in this employment of the device with an appliance interface surface is to provide a bonding surface for adhesive wound drape 100 and for seating appliances that capture fistula and wound effluent 116.

FIG. 8A shows the application of device 70 over fistula 108. Device 70 is sized to have a diameter greater than that of fistula 108; for example, a gap of approximately 6 mm around the margin base of fistula 108 is suitable, although larger and smaller gaps may be used. After placement, as in FIG. 8B, device 70, fistula 108 (covered by device 70) and the entire wound bed 112 are covered with a wound dressing 104, such as open-celled foam, with a cavity 106 formed therein to accommodate device 70. Wound dressing 104 and appliance interface surface 74 are covered and typically sealed with an adhesive wound drape 100 to the surrounding abdominal tissue 110, afterwhich negative pressure or vacuum is typically initiated to compress wound dressing 104 and device 70. A hole 102 may be cut through wound drape 100 to expose vessel opening 46 and provide fluid communication to vessel 72. Typically, an effluent collection appliance is then adhesively bonded to appliance interface surface 74 to seal vessel opening 46 and capture effluent 116.

Figure 9A:
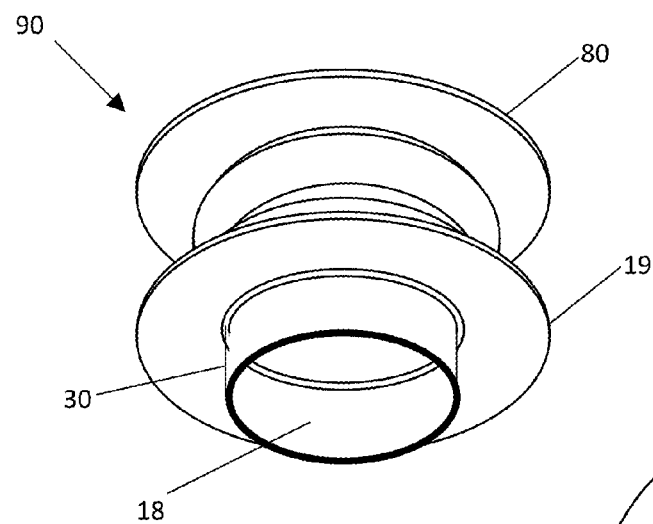
FIG. 9A is a perspective view of an additional alternative embodiment of a device with appliance interface.
Figure 9C:
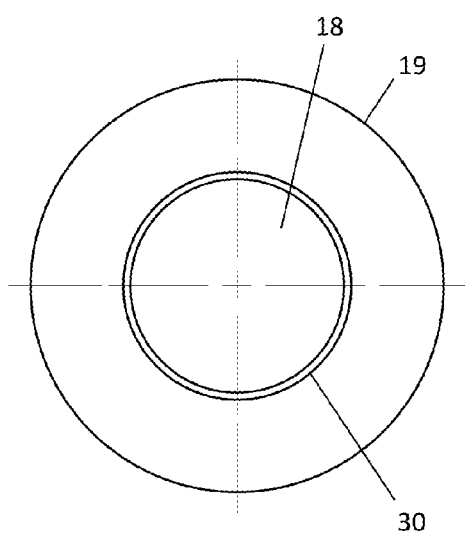
FIG. 9C is a bottom view of the device of FIG. 9A.
Figure 9B:
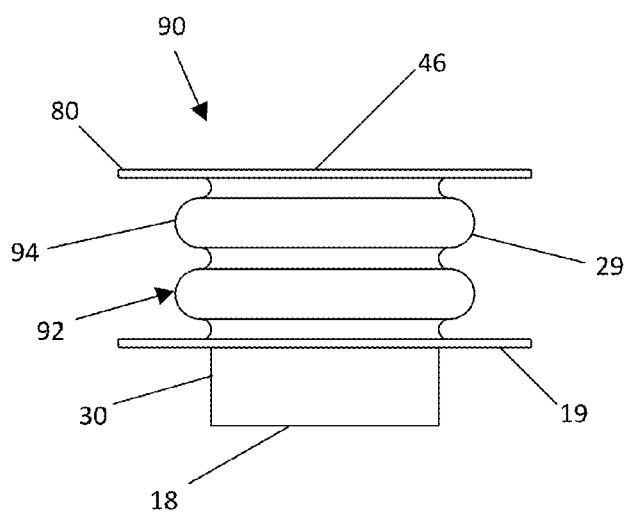
FIG. 9B is a side view of the device of FIG. 9A.

FIGS. 9A, 9B and 9C illustrate another embodiment of a device for enteric effluent management having an appliance interface. Device 90 is designed to collapse symmetrically and maintain form when employed as part of a compression dressing to prevent deformation or buckling over and related aggravation of the fistula or wound.

Device 90 has a flexible fluid containment vessel 92, formed by vessel walls 94 having rounded pleats 29. Vessel 92 has a primary vessel opening 18 configured to fit over a wound or fistula and a secondary vessel opening 46 axially aligned with primary opening 18. Extending radially out from walls 94 at or near vessel opening 18 is a flexible flange 19, which when device 90 is seated on, in or over a fistula, forms a sealing or seating ring around the fistula. Flange 19 can be trimmed as needed. Extending axially from flange 19 is a skirt 30, in most embodiments an annual skirt, which can be trimmed as needed. Extending radially out from walls 94 at or near vessel opening 46 is a flange 80, which creates a surface area for bonding adhesive wound drapes to device 90 and for seating appliances that capture fistula and wound effluent. Flange 80 also can be trimmed as needed.

As one specific exemplary embodiment, sidewall 94 may have a height, between flange 19 and flange 80 of at least 1 inch, for example, about 1½ inches. The inner diameter of vessel 92 and flange 19 at primary vessel opening 18 may be, for example 1 to 1½ inches, or 1¼ to 1½ inches. The inner diameter of vessel 92 and flange 80 at secondary vessel opening 46 may be the same or different than at primary vessel opening 18; for example, the inner diameter of vessel 92 and flange 80 at secondary vessel opening 46 may be 1¼ to 1½ inches. The length of skirt 30 may be, for example, about 0.5 inch (e.g., 0.52 inch), and the thickness of skirt 30 may be, for example, about 0.05 inch. The thickness of either or both flange 19 and flange 80 may be, for example, 0.05 inch. Device 90 may be molded from a polymeric or rubber (e.g., latex rubber) material, so that the entire device 90 is flexible.

The various embodiments of devices described herein may be made of any material suitable for the purposes described above, as will be recognized by those skilled in the art. Thus, in certain embodiments, the enteric fistula healing devices, or at least a portion thereof, may be made of any biocompatible materials, for example, plastics or rubber. In one particular embodiment, the vessel may be a latex rubber. Other materials may be used, for example, an elastomeric acrylonitrile butadiene styrene ("ABS") or urethane. Preferably, at lest the fluid containment vessel is non-fluid permeable and/or non-porous. Further, as will be recognized by those skilled in the art, the devices can be sized and shaped to accommodate all different sizes and shapes of fistulas and/or wounds.

Accordingly, described herein are various embodiments of devices to contain and control the effluent of enteric fistulas; these devices are adaptable to other fistulas, stomas, and other wound types. Described is, for example, a device to contain and control the effluent of enteric fistulas, other fistulas, stomas, and other wounds, the device comprising: (a) a containment vessel having a predetermined cross-sectional shape and size, (b) vessel walls which compress to a predetermined degree when a predetermined pressure is applied, (c) a primary vessel opening of a predetermined size and shape to fit over the wound or fistula being treated, and (d) means for creating a seal around the primary vessel opening at the wound bed interface whereby effluent is contained. Such a device may further include a secondary vessel opening of predetermined size and shape. An integral tube of predetermined length to direct effluent away from the wound site may be present in the secondary vessel opening. Additionally or alternately, an appliance interface of predetermined size and shape to create a bonding surface for wound dressings and effluent collection appliances may be present at the secondary vessel opening. Such a device may further include an internal drainage management tube of predetermined size and shape inserted though the primary vessel opening, the secondary vessel opening and the integral tube; the drainage tube may have perforations of a predetermined size and shape, at a predetermined location. A stopper feature of a predetermined shape and size may be present on the internal drainage management tube to stop travel at the base of the integral tube and/or seal off airflow between the tubes. Any of the previous embodiments may further include a single or plurality of cuttable, flexible skirt(s) concentric to the primary vessel opening of predetermined size and shape that can be custom cut at bedside to best fit, position, seat, and seal the device.

Multiple skirts can define a concentric pressure equalization chamber between two skirts in order to equalize the fluid pressure in the concentric pressure equalization chamber with the high wound fluid pressure inside the device. Equalization is achieved through channels or perforations through an interior seal to the concentric pressure equalization chamber. Equalization of the concentric pressure equalization chamber at the higher wound pressure is desired in order to reduce the draw of effluent from the wound toward the concentric chamber and seal failure when the wound has sudden spikes in effluent fluid pressure.

Also, any of the embodiments may further include a cuttable, flexible flange around the perimeter of the primary vessel opening of predetermined size predetermined size, shape, and surface texture that can be custom cut at bedside to best fit the device to irregular wound beds and positively center the device over a fistula or wound that is in close proximity to the sides of the wound bed or underneath the edges of the abdominal wall. An open-celled foam ring of a predetermined size and shape may be attached to the perimeter of the primary vessel opening to seat the device in the wound bed. Any device may include a chemical or biological coating or impregnation to facilitate wound healing, or may include a biologic membrane held inside the vessel to support the growth of healthy granulation tissue and accelerate fistula and wound closure. As another option, any device may include an electric power supply with electrical leads connected to a biologic membrane or the wound bed to accelerate healing with electrical stimulation. A bulb of a predetermined cross-sectional shape and size may be present on the inside of the vessel to help seal fistulas and wounds. Around the perimeter of the secondary vessel opening may be a cuttable flange of predetermined size predetermined size, shape, and surface texture that can be custom cut at bedside to best fit the device to irregular wound beds and positively center the device over a fistula or wound that is in close proximity to the sides of the wound bed or underneath the edges of the abdominal wall. Any of the devices may include one or a plurality of flexible hooks of predetermined size and shape in the circumference of the primary vessel opening to hook into the mouth of a wound or fistula as a retention mechanism. The device may include a separate wound drape cutter ring of predetermined size and shape which snaps onto the appliance interface to cut wound drape and create a bonding surface for effluent collection appliances.

Additionally, the various embodiments have numerous advantages:
  simple construction so device and dressings can be applied and changed by untrained bedside or homecare nurses;
  positive seals to the wound bed do not allow effluent to be drawn past the seal with NPWT or other wound care techniques which extends dressing life and establishes effective conditions for wound healing;
  skirt design centers and aligns device over a fistula or wound and holds device in the intended location with NPWT and other wound therapies during normal daily activity of the patient;
  seal design and textured flanges mitigate the need for ostomy adhesive which reduces the frequency of wound dressing changes due to ostomy adhesive failure;
  device flanges and skirt can be custom cut at bedside to best fit the device to irregular wound beds and positively center the device over a fistula or wound that is in close proximity to the sides of the wound bed or underneath the edges of the abdominal wall;

devices are flexible and compresses symmetrically when part of NPWT or other wound therapies to prevent deformation or buckling over and related aggravation of the fistula or wound;

devices isolate the fistula or wound from NPWT vacuum thus protecting the bowel or wound site from negative pressures;

devices are less intrusive than plug-type devices which can aggravate fistulas and wounds and cause bowel injury;

devices can incorporate biologic solutions to provide a matrix for the growth of healthy granulation tissue and accelerate fistula and wound closure; and devices improve quality of life by allowing patients to return to their normal life and work routines during the healing process Thus, embodiments of the DEVICES AND METHODS FOR TREATMENT OF FISTULAS AND COMPLEX WOUNDS are disclosed. The implementations described above and other implementations are within the scope of the following claims. One skilled in the art will appreciate that the present invention can be practiced with embodiments other than those disclosed. For example, the device vessel could have other shapes, such as oval, rectangular, etc.; flanges could intersect the vessel at various angles; a plurality of skirts could be added to the circumference of the primary vessel opening; the skirts, whether annular or not, could have other cross-sectional shapes with bulbs, fins, ribbing or pleats; the device could be coated or impregnated with chemical or biological material to accelerate wound healing; etc. The disclosed embodiments are presented for purposes of illustration and not limitation, and the present invention is limited only by the claims that follow.

What is claimed is:

1. A device to manage effluent drainage from a wound such as a fistula, the wound including a wound opening, and a wound bed surrounding the wound opening, the device comprising:
   a liquid containment vessel having a first end and an interior volume defined by a sidewall configured to collapse from a first height to a second height less than the first height, the liquid containment vessel having an outer diameter at the first end, the first end defining a primary vessel opening providing liquid communication between the interior volume and the wound opening;
   a flexible and trimmable annular skirt depending from the first end of the vessel; and
   a wound sealing flange proximate the primary vessel opening, the flange having an outer diameter greater than the vessel outer diameter at the first end,
   wherein the device is configured to be applied to the wound bed such that the sidewall and the skirt surround the wound opening, the skirt at least partially extending around or within the wound opening, and the flange forms a seal around the wound opening, thereby physically isolating the wound opening from the wound bed.

2. The device of claim 1 further comprising a secondary vessel opening at a second end of the liquid containment vessel, the secondary vessel opening providing liquid communication to the interior volume and the primary vessel opening.

3. The device of claim 2 further comprising an appliance interface surface annular to the secondary vessel opening.

4. The device of claim 3 wherein the appliance interface surface has an outer diameter greater than an outer diameter of the vessel at the second end.

5. The device of claim 1 further comprising a second skirt depending from the first end of the vessel encircling the primary vessel opening.

6. The device of claim 1 wherein the sidewall comprises ribs or pleats to facilitate its collapse.

7. The device of claim 1 wherein the sidewall is configured to collapse from a first height of at least 1 inch to a second height less than ½ inch.

8. A device to manage effluent drainage from a wound such as a fistula, the wound including a wound opening, and a wound bed surrounding the wound opening, the device comprising:
   a unitary, non-porous liquid containment vessel having a first end and a second end, and an interior volume defined by a sidewall configured to collapse from a first height to a second height less than the first height, the first end defining a primary vessel opening providing liquid communication between the interior volume and the wound opening;
   a flexible trimmable annular skirt depending longitudinally from the first end of the vessel;
   a secondary vessel opening at the second end providing liquid communication to the interior volume; and
   a wound sealing flange extending radially from the sidewall proximate the primary vessel opening and between the sidewall and the annular skirt, the flange having an outer diameter greater than the vessel outer diameter at the first end,
   wherein the device is configured to be seated in the wound such that the flange forms a sealing ring around the wound opening, thereby physically isolating the wound opening from the surrounding wound bed.

9. The device of claim 8 further comprising a flange forming an appliance interface surface annular to the secondary vessel opening.

10. The device of claim 8 wherein the sidewall comprises radiused pleats to facilitate its collapse.

11. The device of claim 8 wherein the sidewall is configured to collapse from a first height of at least 1 inch to a second height less than ½ inch.

12. The device of claim 8 wherein the containment vessel has a diameter of 1 to 1½ inches.

* * * * *